(12) United States Patent
Benz et al.

(10) Patent No.: US 10,193,956 B2
(45) Date of Patent: Jan. 29, 2019

(54) GROUPING AND TRANSFERRING OMIC SEQUENCE DATA FOR SEQUENCE ANALYSIS

(71) Applicant: Five3 Genomics, LLC, Santa Cruz, CA (US)

(72) Inventors: Stephen Charles Benz, Santa Cruz, CA (US); John Zachary Sanborn, Santa Cruz, CA (US); Charles Joseph Vaske, Santa Cruz, CA (US)

(73) Assignee: FIVE3 GENOMICS, LLC, Santa Cruz, CA (US)

( * ) Notice: Subject to any disclaimer, the term of this patent is extended or adjusted under 35 U.S.C. 154(b) by 1015 days.

(21) Appl. No.: 14/541,068

(22) Filed: Nov. 13, 2014

(65) Prior Publication Data

US 2015/0134662 A1   May 14, 2015

Related U.S. Application Data

(60) Provisional application No. 61/903,903, filed on Nov. 13, 2013.

(51) Int. Cl.
*H04L 29/08* (2006.01)
*G06F 19/22* (2011.01)
*G06F 17/30* (2006.01)
*G06F 19/28* (2011.01)

(52) U.S. Cl.
CPC ........ *H04L 67/06* (2013.01); *G06F 17/30076* (2013.01); *G06F 19/22* (2013.01); *G06F 19/28* (2013.01)

(58) Field of Classification Search
None
See application file for complete search history.

(56) References Cited

U.S. PATENT DOCUMENTS

| 7,743,233 | B2 | 6/2010 | Wang et al. |
| 2003/0211504 | A1 | 11/2003 | Fechtel et al. |
| 2007/0020651 | A1 | 1/2007 | Frudakis |
| 2009/0170717 | A1 | 7/2009 | Agan et al. |
| 2011/0288785 | A1 | 11/2011 | Tembe |
| 2012/0095693 | A1 | 4/2012 | Ganeshalingam et al. |
| 2012/0233201 | A1 | 9/2012 | Ganeshalingam |
| 2012/0236861 | A1 | 9/2012 | Ganeshalingam |
| 2014/0278461 | A1 | 9/2014 | Artz |

FOREIGN PATENT DOCUMENTS

WO    2013/009890    1/2013

OTHER PUBLICATIONS

ISA/KR, International Search Report and Written Opinion, Int'l Appln No. PCT/US2014/065562, dated Feb. 25, 2015 (18 pages).
Turro, Ernest, "RNA-Seq Mapping Practical," University of Cambridge, Oct. 29, 2012, 6 pages.

(Continued)

*Primary Examiner* — G Steven Vanni
(74) *Attorney, Agent, or Firm* — Umberg Zipser, LLP

(57) ABSTRACT

"Omic" digital data transport systems and methods are disclosed. The disclosed systems and methods employ a transport server that assembles a transport group larger numbers of omic output files on the basis of machine specific annotation from one or more sequencing devices and user input related to one or more attributes for the omic output files.

10 Claims, 1 Drawing Sheet

(56) References Cited

OTHER PUBLICATIONS

Anonymous: "Massive parallel sequencing—Wikipedia", , Oct. 9, 2013 (Oct. 9, 2013), XP055392779, 4 pages Retrieved from the Internet: URL:https://en.wikipedia.org/w/index.php?title=Massive_parallel_sequencing&oldid=576455180.

Anonymous: "Merge lanes while preserving the read group info—GATKForum", , Jun. 30, 2013 (Jun. 30, 2013), XP055392758, 1 page Retrieved from the Internet: URL:https://gatkforums.broadinstitute.org/gatk/discussion/2730/mergelanes-while-preserving-the-read-group-info.

EPO, Extended European Search Report for EP Application No. 14862192.3, dated Aug. 1, 2017 (8 pages).

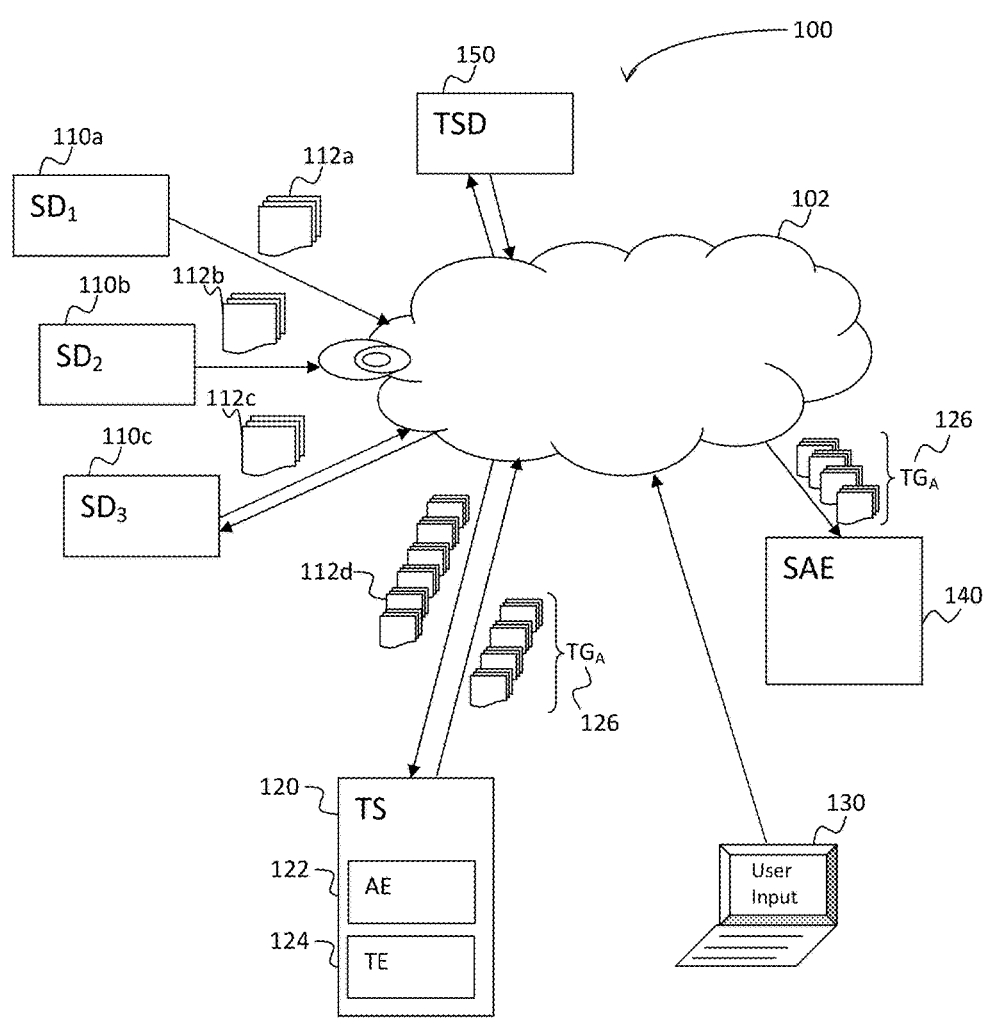

GROUPING AND TRANSFERRING OMIC SEQUENCE DATA FOR SEQUENCE ANALYSIS

This application claims priority U.S. provisional application Ser. No. 61/903,903, filed on Nov. 13, 2013. U.S. Provisional Application No. 61/903,903 and all other extrinsic references referenced herein are incorporated by reference in their entirety.

FIELD OF THE INVENTION

The field of the invention is systems and methods of transmission and pre-processing of genomic sequencing data, especially as it relates to annotation, queuing, and mass transfer of genomic sequencing files from one or more sequencers to a sequence analysis engine.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

With increasing sample throughput in sequencing devices, the volume and transmission speed of genomic data is bound to become a limiting factor in the analysis of whole genomes. For example, many modern sequencing devices have a throughput of 1-20 Gbp/day and it can be reasonably expected that new sequencing technologies will increase this throughput even further. Unfortunately, current protocols for data delivery to sequence analysis engines are at least in some cases no longer able to efficiently handle such data volume and will ultimately slow down processing speed, and with that delay sequence analysis and potentially patient care.

To overcome difficulties associated with routing biological sequence information, one or more network nodes may include a packet generator that generates a data packet including a first header containing network routing information and a second header with attributes associated with a layered data model of existing knowledge representative of the biological sequence data as described in US 2012/0236861 and US 2012/0233201. Handling of high volumes of sequence information in a facility is described in US 2014/0278461. However, none of the known systems and methods is especially suitable to manage vast quantities of data in a manner that would streamline subsequent analysis, especially as such analysis relates to particular analysis needs or requirements by a medical professional.

Clearly, even though numerous manners of handling sequence information are known in the art, new modes of data handling are required that allow to take full advantage of the recent advances in sequencing technology.

SUMMARY OF THE INVENTION

The inventive subject matter is drawn to various systems and methods in which multiple omic sequences from one or more data sources (e.g., sequencing device) are fed to a transport server that pre-processes and groups the sequences into a transport group that is then routed to a sequence analysis engine. In especially preferred aspects, pre-processing and grouping is done on the basis of machine-specific annotations in the omic sequences and an annotation input from a user. In that way, the omic sequences can be grouped in real time, and routed to a downstream sequence analysis engine. As the omic sequences are preferably grouped such that all sequences required for sequence analysis are in a single transport group (i.e., in one logical unit), delays associated with interrupted sequence analysis (e.g., due to lack of one or more sequences for analysis or time spent loading missing sequences) are reduced, and more typically entirely avoided. Such advantage is particularly beneficial where the sequence analysis engine is used to process numerous omic data from numerous users and/or patient samples. Viewed from a different perspective, the systems and methods contemplated herein allow a sequence analysis engine to operate at maximum speed as all data relevant for an analytic task by the sequence analysis engine are provided in a single group or matching/corresponding groups.

In one aspect of the inventive subject matter, the inventors contemplate a transit system for delivery of a plurality of omic sequences that includes a transport server comprising a transit engine and an annotation engine. Most preferably, the transport server is coupled to one or more sequencing devices that provide multiple omic output files to the transport server, wherein each of the omic output files comprises sequence data and a machine-specific annotation, and the transport server is further coupled to a sequence analysis engine (e.g., BAM server) that receives a transport group from the transport server. In especially preferred aspects, the annotation engine annotates the omic output files using an annotation input from a user to so form annotated omic output files, and the transit engine groups the annotated omic output files into the transport group based on both, the machine-specific annotation and the annotation input from the user. The transit engine then transfers the transport group to the sequence analysis engine.

While not limiting to the inventive subject matter, it is generally preferred that the omic output files are genomic output files (e.g., whole genome or exome), RNA-omic output files, or proteomic output files, and where the output file is a nucleotide sequence, it is preferred that the genomic output file is in SAM format, BAM format, VCF format, FASTQ format, and FASTA format. In addition, it is contemplated that the system will also include a temporary data storage device coupled between the plurality of sequencing devices and the transport server, and that the sequencing devices provide the omic output files to the transport server via the temporary data storage. Where desired, it is also contemplated that at least one of the sequencing devices is configured to receive a feedback signal from the transport server and/or the sequence analysis engine.

In further contemplated aspects, the machine-specific annotation comprises an annotation that includes a date and/or time identifier, a sequencing device identifier, a lane identifier, a quality score, and/or pair member identifier, and the annotation input from the user will typically include an analysis type annotation (e.g., whole genome analysis, exome enrichment analysis, transcriptome analysis, and proteome analysis) and/or a patient specific annotation (e.g., patient identifier, a tissue identifier, a tissue status identifier, and a health record identifier).

Most preferably, but not necessary, it is contemplated that the transit engine will group the annotated omic output files in real time, and/or that the transit engine will group the annotated omic output files independent of actual sequences in the annotated omic output files. In further contemplated aspects, the transit engine will transmit the transport group upon completion of forming the transport group, or may use a predetermined grouping mode for a machine-specific annotation. Where desired, it is also contemplated that the transit engine encrypts the transport group, and/or provides or adds a unique ID to the transport group. Thus, the transport server may receive the omic output files from the sequencing devices in an encrypted form, optionally upon request to the sequencing devices.

Consequently, the inventors also contemplate a method of transferring multiple omic sequences in which a transport server having a transit engine and an annotation engine is provided. The transport server then receives multiple omic output files from respective multiple sequencing devices, wherein each of the omic output files includes sequence data and a machine-specific annotation. The annotation engine is then used by a user to annotate the omic output files to so form annotated omic output files, and the transit engine then groups the annotated omic output files into a transport group, preferably in real time. Most preferably, the grouping will be based on both, the machine-specific annotation and the annotation input from the user. Finally, the transport server will then deliver the transport group to a sequence analysis engine (e.g. BAM server).

As noted before, omic output files may be have numerous types of content, but are typically genomic output files (e.g., exomes, whole genome, etc.), RNA-omic output files (e.g., transcriptome), or proteomic output files, which will preferably converted from a raw format into a SAM format or a BAM format. Where desired, the omic output files may be temporarily stored in a data storage device prior to the step of receiving the plurality of omic output files by the transport server. Additionally, it is contemplated that the transport server may provide a feedback signal to one or more of the sequencing devices and/or the sequence analysis engine.

It is further generally preferred that the machine-specific annotation include a date and/or time identifier, a sequencing device identifier, a lane identifier, a quality score, and/or pair member identifier, and/or that the annotation input from the user includes analysis type annotation (e.g., whole genome analysis, exome enrichment analysis, transcriptome analysis, and proteome analysis) and/or a patient specific annotation (e.g., patient identifier, a tissue identifier, a tissue status identifier, and a health record identifier). In addition, it is contemplated that the transport group is delivered upon completion of forming the transport group, or upon a predetermined delivery schedule or protocol. Where desired, it is also contemplated that the transit engine will provide or add a unique ID to the transport group.

Therefore, viewed from another perspective, the inventors also contemplate a method of transferring omic sequences in which a transport server receives multiple omic output files, each comprising sequence data and a machine-specific annotation. The omic output files are then grouped into a transport group using an annotation input from a user in addition to the machine-specific annotation. The transport group is then transferred from the transport server to a downstream analytic device (e.g., BAM server).

While not limiting to the inventive subject matter, it is preferred that the grouping is performed independently of the sequence data, and even more preferably in real-time. Moreover, it is contemplated that the annotation input from the user includes an analysis type annotation (e.g., whole genome analysis, exome enrichment analysis, transcriptome analysis, and proteome analysis) and a patient specific annotation (e.g., patient identifier, a tissue identifier, a tissue status identifier, and a health record identifier). As already noted above, it is generally preferred that the transport group is transferred from the transport server to the downstream analytic device upon completion of the transport group. Where desired, the omic output files may be provided by a database storing omic output files or by a plurality of sequencing devices.

Viewed from yet another perspective, the inventors also contemplate a method of reducing processing time for genomic analysis in a sequence analysis engine. In especially preferred methods, a transport server produces a transport group from a multiple omic output files, wherein the omic output files are grouped according to a machine-specific annotation and an annotation input from a user. The sequence analysis engine (e.g., BAM server) then receives the transport group and processes the transport group as a logical unit.

Most typically, the omic output files in the transport group will have a SAM format or a BAM format, and the annotation input from the user includes an analysis type annotation (e.g., whole genome analysis, exome enrichment analysis, transcriptome analysis, and proteome analysis) and/or a patient specific annotation (e.g., patient identifier, a tissue identifier, a tissue status identifier, and a health record identifier).

Various objects, features, aspects and advantages of the inventive subject matter will become more apparent from the following detailed description of preferred embodiments, along with the accompanying drawing FIGURES in which like numerals represent like components.

BRIEF DESCRIPTION OF THE DRAWING

FIG. 1 is an exemplary illustration of a transmission and pre-processing system for omics sequences according to the inventive subject matter.

DETAILED DESCRIPTION

It should be noted that any language directed to a computer should be read to include any suitable combination of computing devices, including servers, interfaces, systems, databases, agents, peers, engines, controllers, modules, or other types of computing devices operating individually or collectively. One should appreciate the computing devices comprise a processor configured to execute software instructions stored on a tangible, non-transitory computer readable storage medium (e.g., hard drive, FPGA, PLA, solid state drive, RAM, flash, ROM, etc.). The software instructions preferably configure or program the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps. In some embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

As used in the description herein and throughout the claims that follow, when a system, engine, server, device, module, or other computing element is described as configured to perform or execute functions on data in a memory, the meaning of "configured to" or "programmed to" is defined as one or more processors or cores of the computing element being programmed by a set of software instructions stored in the memory of the computing element to execute the set of functions on target data or data objects stored in the memory.

One should appreciate that the disclosed techniques provide many advantageous technical effects including configure one or more computing devices to process omic data efficiently by organizing the omic-data into computational logical units.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

The inventors have now discovered that sequence analysis for numerous omics sequences provided by one or more data sources and delivered to a sequence analysis engine can be readily improved by pre-processing and/or grouping of the omics sequences to so form logical units that are then fed to the sequence analysis engine, and that are processed without the need for retrieval of further sequences required for the same analysis. It should be especially noted that such pre-processing and/or grouping will significantly reduce processing time required by the sequence analysis engine, and may also significantly reduce the time to completion where the sequence analysis was compromised by invalid and/or missing data as such data can be requested and sent to the sequence analysis engine in an efficient and coordinated manner.

In particularly preferred aspects of the inventive subject matter, pre-processing and/or grouping is performed using both, machine-specific annotations and user annotation(s). Viewed from another perspective, the inventors contemplate a transport server that lines up and/or groups multiple omics sequences for analysis based on user and (sequencing) device parameters without regard to the actual omic sequences being transmitted. Therefore, and viewed from a different perspective, a user will be able to set up a user-defined rule for sequence analysis, in which the rule determines the real-time grouping of the omics output files into one or more transport groups.

For example, FIG. 1 exemplarily illustrates a transit system 100 for delivery of a plurality of omic sequences from a number of sequencing devices to a sequence analysis engine. Most typically, the omic sequences comprise sequence data (e.g., nucleic acid sequences) and a machine-specific annotation. Here, system 100 comprises multiple sequencing devices 110a, 110b, and 110c that produce from a plurality of patient samples, which may be from the same or different patient (not shown) a plurality of omic output files 112a, 112b, and 112c. In most cases, the sequencing devices 110a, 110b, and 110c are informationally coupled to the transport server 120 via wide area network 102, and all of the omic output files 112d are directly or indirectly (e.g., via temporary data storage device 150) routed to the transport server 120. Example sequencing device include Oxford Nanopore MinION, or any of the Illumina® MiSeq or HiSeq devices.

Most preferably, contemplated systems include a transport server 120 that includes an annotation engine 122 and a transit engine 124, and the transport server 120 is coupled via wide area network 102 to the sequencing devices 110a-110c so that the sequencing devices can provide respective omic output files to the transport server. The transport server is also coupled via wide area network 102 to a sequence analysis engine 140 that receives from the transport server 120 via the wide area network 102 a transport group 126 from the transport server. Annotation engine 122 is preferably configured to annotate the omic output files using an annotation input from an input device 130 of user (e.g., medical professional) to so form annotated omic output files 126. The transit engine 124 is configured (most typically via one or more predefined rules) to group the annotated omic output files into the transport group based on the machine-specific annotation and the annotation input from the user. Once grouped, the transit engine then transfers the transport group to the sequence analysis engine 140 (e.g., BAM server).

Although the transport server 120, the sequence analysis engines 140, and input device 130 are illustrated as individual computing devices, it should be appreciated that the each device could take on different forms. In some embodiments, the collection of devices could be implemented as a cloud-based service; perhaps a for-fee service. Stakeholders (e.g., insurance companies, physicians, oncologists, pharma companies, patients, other analysis engines, etc.) can subscribe to the services. The services can be provided via web services interfaces (e.g., WSDL, SOAP, HTTP, REST, BEEP, etc.) possibly through a network accessible API. In other embodiments, the devices can be a singular devices having one or more applications installed on the computing devices. Still further, in other embodiments, the devices can comprise a single, unitary device providing all the rules or responsibilities for the three devices.

In one exemplary aspect of the inventive subject matter, a user has provided (directly or indirectly) a sequencing facility with one or more samples (e.g., a tumor sample and a matched normal sample from the same patient) for whole genome analysis. The user then uses a suitable security measure (e.g., a one-time use key that is preferably linked to the sequence reads) to access the sequencing facility for download, while the sequencing facility will typically use a corresponding security measure (e.g., same or matching key) for upload to the user. Most typically, the sequence information will be encrypted in at least one segment of transport. For example, the sequence information may be encrypted by an encryption module of the sequencing device, or an encryption device that is informationally coupled to the sequencing device. While it is generally contemplated that the sequencing devices will be co-located in a single sequencing facility, it should be recognized that co-location is not critical to the inventive subject matter.

With respect to suitable sequencing devices it should be appreciated that the particular type of sequencing device is not limiting to the inventive subject matter, but that all devices that produce an omic output are deemed suitable for use herein. However, especially preferred devices include nucleic acid sequencing devices that provide genomic raw data, or genomic data converted to SAM format, BAM format, VCF format, FASTQ format, or FASTA format. In addition, proteomics high throughput devices and RNA analysis devices are also contemplated herein. While it is contemplated that a patient sample can be exclusively analyzed on a single sequencing device, it is also contemplated that the sample can be analyzed using two or more different sequencing devices. Still further, it is contemplated that the sequencing devices may also be configured to receive one or more feedback signals from the transport server, sequence analysis engine, and/or user via the user input device. For example, where the sequence analysis engine determines that certain regions in the genome require a higher reading threshold, the sequence analysis engine may provide feedback to the transport server and/or sequencing device to perform further analysis for that region. On the other hand, where the transport engine determines that a device parameter of a particular sequencing device fails to satisfy a specific predetermined level (e.g., data of one or more lanes below predetermined quality score), the transport engine may provide instructions to the sequencing device to change an operational parameter or to go offline. Therefore, and regardless of the particular type of sequencing device, it is contemplated that the device will (preferably automatically) attach to the omic output file a machine-specific annotation. For example, suitable machine-specific annotations include a date and/or time identifier, a sequencing device identifier, a lane identifier, a quality score, and/or a pair member identifier.

With respect to security, the data flowing through transit system 100 can be secured through multiple techniques. In some embodiments, the omic data can be sent over secure communication links, possibly via secure FTP, HTTPS, SSL, or other protocol. In general, higher strength implementations of cryptographic protocols or algorithms are more preferred. However, the computational overhead or other cost associated with cryptographic protocols can dictate using less secure implementations of cryptographic protocols or algorithms. For example, AES-128 might be sufficient for most consumers, AES-256 or higher levels of AES could be used for circumstances where confidentiality is of greater import than computational costs. Further, the omic data can be stored within secured memories, possibly memories or storage modules that adhere to one or more levels of FIPS-140. Additional other suitable algorithms include 3DES, Twofish, Blowfish, XXTEA, PGP, or other known algorithms or those yet to be invented. It should be appreciated that at least some data from the omics files, a sequence of a patient's genome, could form a basis for a token or key with respect to the implementations of the cryptographic protocols or algorithms. Thus, only an entity having access to the patient's omic data could unlock or gain access to the data.

Thus, it should be recognized that the data source(s) that provide the omic data will in most cases automatically annotate the omic data using device-specific parameters, and that such annotation will be in a predefined format. For example, a typical sequencing device will provide sequencing data in FASTQ or FASTA format, and as such include an instrument name, flowcell ID and/or name, index number for a multiplexed sample, indication as to the member of a pair (for paired-end or mate pair reads), etc. Additionally, the device-specific parameters may also include a quality value with respect to the read, and where desired optional sequence annotations (e.g., sequence identifier and/or description). Of course, it should be recognized that the data source(s) may provide the omic data directly in a streaming fashion, or from an intermediary data storage, or even from a temporary data storage device that is coupled between the sequencing device(s) and the transport server.

Regardless of the type of omic data source and manner of data delivery, it is typically preferred that the raw sequence data output files are converted to a file type that is suitable for analysis by the sequence analysis engine. In especially preferred aspects of the inventive subject matter, the file type for the sequence analysis engine is a SAM or BAM file. There are numerous file converters/aligners known in the art, and exemplary converters/aligners to convert a FASTQ to a SAM or BAM file include Bowtie, BWA, GAR, Bfast, Maq, Mosaik, Novoalign, or Ssaha2, etc. Where the output is a SAM file, it should be appreciated that such file can be converted to the corresponding BAM file using SAMtools. Of course, it should also be noted that the conversion of the sequencing device raw data to SAM or BAM files can be done at any location upstream of the sequence analysis engine. However, it is generally preferred that the conversion of the raw data to SAM or BAM files is performed at or upstream of the transport server such that the transfer group is a group of SAM or BAM files.

In a typical example, the user will operate a dedicated transport server via a user input device (e.g., computer or mobile device connected to a wide area network), which may be co-located with the user, or may be remotely located and accessed by the user via a terminal or other appropriate interface. Regardless of the location of the transport server, it is contemplated that the user will annotate the omic output files (e.g., sequence reads) from the data source (e.g., sequencing device) using an annotation input that is specific to the upload of the omic data. In most instances, the transport server will include an annotation engine to allow the user to perform such annotation. However, annotation may also be provided via a separate annotation module that is then coupled to the transport server. While the nature of the annotation input is not limiting to the inventive subject matter, it should be appreciated that the annotation input will typically bear at least some significance to the sample and/or patient, and most typically include an analysis type annotation and a patient specific annotation.

For example, the analysis type annotation may be specific to the particular protocol or technique used for sample preparation, sample procedure, etc., and thus may include reference to whole genome analysis, exome enrichment analysis, transcriptome analysis, proteome analysis, etc. Likewise, the patient specific annotation will generally relate to some information that is at least to some degree associated with the patient. For example, patient specific annotation will typically include a patient identifier, a tissue identifier, a tissue status identifier (e.g., matched normal, diseased, primary tumor, recurring tumor, metastatic tumor, etc.), a health record identifier (e.g., type of disease, status of patient), electronic medical record identifier, etc. User annotation may further include the type of desired analysis (e.g., a request to compare tumor versus matched normal, or tumor versus earlier tumor sample or other reference).

Thus, it should be recognized that the user will provide a second layer of information to the omics data that will allow association of the omics information with information that is uniquely relevant to the patient, the specific type of patient sample (e.g., diseased versus control, or before and during/after treatment with a drug) type of analysis ordered (e.g., whole genome analysis or exome or transcriptome analysis). Such dual information content (i.e., machine-specific annotation and the annotation input from the user) is particularly beneficial where numerous sequencing runs must be coordinated for subsequent analysis. Once properly grouped, analysis can be performed with minimal interruptions that would otherwise be due to missing or incomplete omics information. Most typically, the transit engine will be configured to transmit the transport group upon completion of forming the transport group as defined by the user (and appropriate rules governing grouping function). On the other hand, grouping according to a predetermined grouping mode for machine-specific annotation is also contemplated.

Grouping is typically performed at the transport server using the transit engine and both the user annotation and the machine-specific annotation such that a group of sequences is formed that is a complete group of sequences with respect to a particular analytic task by the sequence analysis engine. Therefore, in at least one aspect of the inventive subject matter, grouping may be driven by matching normal and diseased sample, which may be refined by matching genomic regions between the samples, or by specific patient, or patient history, as well as by disease type using different patient samples. Matching may further be driven by quality measures of the omic output file and other machine-specific annotations (e.g., exclusion of omic files coming from a particular lane or device). It is further contemplated that the grouping may be performed using an a priori or default grouping that is based on the machine-specific annotations, which may then be modified or tuned on the basis of the user annotations. Thus, it should be appreciated that the grouping of the annotated omic output files can be performed independent of actual sequences in the annotated omic output files, but as a function of specific requirements by a user (e.g., as a function of a desired type of analysis, patient history, type of disease, etc.)

Additionally, it is contemplated that grouping may be driven or modified by a feedback signal from the sequence analysis engine and/or the omic data source. For example, the sequence analysis engine may provide feedback to the transport server to include additional omic data for a particular genomic region, or the omic data source may provide feedback to the transport server that no further omic data are being delivered. On the other hand, the transport server may also provide feedback to the omic data source to repeat a particular analysis, or to the sequence analysis engine to indicate presence or absence of particular data. Regardless of the flow of information and/or grouping, it should be noted that grouping of the omic data into transport groups is performed independently of the actual sequence content, but is merely done on the basis of machine-specific annotation and user annotation (and non-sequence information in the SAM or BAM file). Additionally, it should be noted that the grouping is preferably performed in substantially real-time (i.e., as omics data are delivered or made available), that the groups are sent to the sequence analysis engine with a group-specific ID, and that the group is sent only upon completion of the grouping by the transport server. It should be noted that the transport group is preferably encrypted prior to delivery to the sequence analysis engine.

User annotations can take on many different forms or a broad spectrum of information depending on the nature of the of analysis project at hand. Further the nature of the user annotation can depend on the role or responsibilities of the user with respect to the analysis ecosystem. Consider, for example, where the user has the role of a system administrator of the transport server 120 or the sequence analysis engine 140. The system administrator might create an annotation indicating available network bandwidth or storage capacity. The transport server 120 can package omic data to ensure the resulting logical unit respects such limitation. Alternatively, the user could be a physician. In such a case, the physician might include a user annotation that comprises the physician's unique identifier (e.g., physician registry identifier, national provider identifier (NPI), etc.), a diagnosis code (e.g., ICD-9, ICD-10, DSM, etc.), procedure codes (e.g., CPT, etc.), or other physician related information. Such information can then be used to group the omic data so that they have common attributes; the physician might request that all of their patients be processed in bulk together according to the physician's subscription plan to the services provided by system 100. Additional user annotations could include insurance coverage, urgency information, priority information, data ownership information, or other attributes. In some embodiments, the user annotations could be normalized according to an a priori defined a user annotation namespace or ontology where each type of user annotation could comprise attributes (i.e., a dimension in the namespace) that take on specific values (i.e., a metric for the dimension).

Machine-specific annotations, in a similar vein to the user annotations, can also take on a broad spectrum of values to reflect the nature of one or more specific machines or their corresponding states. Thus, the machine-specific annotations could pertain to one or more devices within ecosystem 100, including sequencing devices 110a through 110c, transport server 120, input device 130, or even sequencing analysis engine 140. Example machine-specific annotations could include device identifiers (e.g., IP addresses, MAC addresses, serial numbers, model numbers, etc.), device bandwidth (e.g., Gpb/second, network bandwidth, etc.), analysis metrics, available machine learning or analysis algorithms, device location, costs to process, CPU availability (e.g, MFLOPs, available threads, available cores, etc.), or other machine-related attributes. Just as user annotations could adhere to a user annotation namespace or ontology, the machine-specific annotations could adhere to a machine attribute namespace. The machine specific annotations can be compiled according to the machine attribute namespace as a machine-specific annotation data structure (e.g., a vector, a tuple, etc.). The annotation engine 122 can thus tag or bind the output files with the data structure, possibly as metadata in the form of an XML file. In some embodiments, the roles or responsibility of the annotation engine 122 can be integrated into sequence devices 110a through 110a, possibly even as an after market adapter.

The transit engine 124 is configured to execute one or more software instructions that embody rules according to which the output files are grouped together. The rules can be provided by the user via input device 130 or could be installed within transport server 120. The rules can be implemented as script or other code that operates based on the user and machine-specific annotations. For example, transit engine 125 could comprise a script-based run-time (e.g., Python, Ruby, Java, .NET, etc.) that provides an API capable of accessing output files 112a through 112c as well as their corresponding annotations. A user can then write a script, or otherwise cause a script to execute, via the APIs, to process the output files in order to building transport group 126. The rules can include requirements, conditions, or other criteria that depend on the annotations or their values, possibly based on the a priori defined namespaces. A simple example could include rules that seek to bind all output files that correspond to a specific physician. The transit engine 124 queries, according to the physician-based rule, for all output files having the physician's identifier. The results set could then be compiled together to form a single logical unit representing that physicians requested work product. It should be appreciated that the rules or scripts could comprise quite complex rules that govern grouping the output files into transport group 126.

It should be appreciated that transport group 126 is considered to be a single logical unit with respect to processing the output files. This approach is considered quite advantageous because it enables the computing devices to optimize computational resources from both a global perspective (e.g., with respect to all files) while also respecting local efficiencies (e.g., very specific requests). Thus, rules or scripts under which the transit engine 124 operates can be considered as the definition of a logical unit processing as defined with respect to the annotations. As an example consider a scenario where system 100 comprises a for-fee genomic processing service available for oncologists. An oncologist could submit an urgent request (i.e., a user annotation with an urgency level, a high dollar value request, a time deadline, etc.) to the system to identifying a known drug that might have a positive impact on the patient's immediate car. In response, the transit engine 124 can identify all output files having the patient identifier and output files relating to reference genomes associated with one or more known drugs. Further, the transit engine 124 can determine which files might require additional reads or data based sequence device annotations. Yet further, the transit engine 124 can use device attributes associated with one or more of sequence analysis engine 140 and that could include device availability or capacity. If sufficient capacity is available, the transit engine 124 can group the related output files together as a logical unit, possibly tagged with the urgency level, and submit the logical unit to the sequence analysis engine 140 for immediate processing. The logical unit could be transmitted as a binary file, a text file, or even a serialized file (e.g., XML, YAML, JSON, etc.) or other format.

In view the transit engine 124 can combine output files together as a logical unit to address optimization needs of system 100 or a stakeholder, one should further appreciate that logical units can be constructed to address myriad possible optimization metrics. Example metrics that could represent a goal or concern for processing transport group 126 include monetary cost, bandwidth, network or processing latency, geographical constraints, security or confidentiality levels, electrical power consumer costs, priority, urgency, importance, patient life expectancy, or other metrics.

With respect to the sequence analysis engine, it is generally contemplated that all known sequence analysis engines are deemed suitable for use herein. However, it is especially preferred that the sequence analysis engine is configured to use a SAM or BAM file as an input file (e.g., BAMserver), and particularly preferred sequence analysis engines include those that produce a local alignment by incrementally synchronizing the first and second sequence strings using a known position of at least one of plurality of corresponding sub-strings, wherein the local alignment is used to generate a local differential string between the first and second sequence strings within the local alignment. Such local differential string is then used to update a differential genetic sequence object in a differential sequence database. Examples for such sequence analysis engines are described in US 2012/0066001, WO 2013/074058, and WO 2014/058987, all of which are incorporated by reference herein.

While it is generally preferred that the systems and methods presented herein are run in continuous or streaming fashion, it is also expressly contemplated that at least some of the omics information in transit may be (typically transiently or temporarily) stored in a data storage device. For example, where patient samples are processed in different devices or even locations, or where one or more sequencing devices are subject to servicing or inoperable for a time, a temporary data storage device may be coupled between the sequencing devices and the transport server to so allow for buffering. One possible example of a temporary buffer could include a personalized genomic data card having a large capacity memory (e.g., preferably greater than 200 GB, 500 GB, 1 TB, 2 TB, or more) and a processor. The personalized data card can store one or more omic output files of the patient that owns the card. For example, the patient's card could comprise a solid state disk drive having a credit card contact pad. As the patient moves through the healthcare system, they can authorize the transport server or other entity to access their genomic data on the car. On the other hand, longer term storage may be implemented in cases where the same patient is subject to testing over a prolonged period of time (e.g., prior to treatment and after treatment/follow-up). Example long term storage solutions include a SAN, NAS, RAID, cloud-based storage, a clinical operating system data custodian, or other type of storage. In some embodiments, the transit system 100 can include one or more a sample database, possibly including a file system, configured to store sequences of the patient's samples.

Therefore, it should be recognized that the inventors contemplate a transit system for delivery of multiple omic sequences (typically DNA, RNA, or protein) will include a transport server having a transit engine and an annotation engine. The transport server is typically (directly or indirectly) coupled to one or more sequencing devices that provide omic output files (comprising sequence data and a machine-specific annotation) to the transport server, and a sequence analysis engine that receives a transport group from the transport server. In especially preferred systems, the annotation engine is configured to annotate the plurality of omic output files using an annotation input from a user to thereby form annotated omic output files, and the transit engine is configured to group the annotated omic output files into the transport group based on the machine-specific annotation and the annotation input from the user. The transit engine is configured to transfer the transport group to the sequence analysis engine.

Viewed from a different perspective, the inventors therefore also contemplate a method of transferring omic sequences using a transport server having a transit engine and an annotation engine. Especially contemplated methods include a step of receiving, by the transport server, omic output files (e.g., genomic output files, RNA-omic output files, or proteomic output files) from sequencing devices, wherein each of the omic output files comprises sequence data and a machine-specific annotation. In another step, the annotation engine annotates the omic output files using annotation input from a user to so form annotated omic output files, and the transit engine groups the annotated omic output files into a transport group, wherein grouping is based on the machine-specific annotation and the annotation input from the user. Finally, the transport server delivers the transport group to a sequence analysis engine.

Thus, it should also be recognized that the inventors contemplate a method of transferring omic sequences in which a transport server receives multiple omic output files comprising sequence data and a machine-specific annotation. The omic output files are then grouped into a transport group using an annotation input from a user and the machine-specific annotation, and the transport group is then transferred from the transport server to a downstream analytic device.

Such group transfer will advantageously lead to a method of reducing the processing time for genomic analysis in a sequence analysis engine in which a transport server produces a transport group from multiple omic output files, wherein the omic output files are grouped according to a machine-specific annotation and an annotation input from a user. The sequence analysis engine then receives the transport group, wherein the sequence analysis engine processes the transport group as a logical unit.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of transferring a plurality of omic sequences, comprising:
   providing an access to a first computer coupled with a second computer;
   receiving, by the first computer, a plurality of omic output files from a plurality of respective sequencers, wherein each of the omic output files comprises sequence data and a machine-specific annotation;
   annotating, by the first computer, the plurality of omic output files using an annotation input from a user to thereby form annotated omic output files;
   grouping, by the first computer, the annotated omic output files into a transport group, wherein grouping is based on the machine-specific annotation and the annotation input from the user and wherein all of the plurality of omic sequences required for sequence analysis are in the transport group;
   delivering, by the first computer, the transport group to the second computer; and
   sending, by at least one of the first and second computers, a feedback signal to at least one of the plurality of sequencers to modify an operation of the sequencer.

2. The method of claim 1 wherein the omic output files are genomic output files, RNA-omic output files, or proteomic output files.

3. The method of claim 1 wherein the operation further comprises converting the plurality of omic output files from a raw format into a SAM format or a BAM format.

4. The method of claim 1 wherein the operation further comprises temporarily storing the plurality of omic output files in a memory prior to the step of receiving the plurality of omic output files by the first computer.

5. The method of claim 1 wherein the at least one of the plurality of sequencers receive another feedback signal from the second computer.

6. The method of claim 1 wherein the machine-specific annotation comprises an annotation selected from the group consisting of a date and/or time identifier, a sequencing device identifier, a lane identifier, a quality score, and a pair member identifier.

7. The method of claim 1 wherein the annotation input from the user comprises an annotation selected from the group consisting of an analysis type annotation and a patient specific annotation.

8. The method of claim 7 wherein the analysis type annotation is selected from the group consisting of a whole genome analysis, exome enrichment analysis, transcriptome analysis, and proteome analysis.

9. The method of claim 1 wherein the step of grouping is performed in real time.

10. The method of claim 1 wherein the step of delivering the transport group is performed upon completion of forming the transport group.

* * * * *